(12) United States Patent
Takamatsu et al.

(10) Patent No.: US 11,485,754 B2
(45) Date of Patent: Nov. 1, 2022

(54) CYCLIC-DI-AMP SODIUM SALT CRYSTAL

(71) Applicant: Yamasa Corporation, Choshi (JP)

(72) Inventors: Misaki Takamatsu, Choshi (JP); Ko Yoshida, Choshi (JP); Marie Matsunaga, Choshi (JP); Kazuya Ishige, Choshi (JP)

(73) Assignee: Yamasa Corporation, Choshi (JP)

( * ) Notice: Subject to any disclaimer, the term of this patent is extended or adjusted under 35 U.S.C. 154(b) by 0 days.

(21) Appl. No.: 17/290,361

(22) PCT Filed: Oct. 31, 2019

(86) PCT No.: PCT/JP2019/042706
§ 371 (c)(1),
(2) Date: Apr. 30, 2021

(87) PCT Pub. No.: WO2020/090948
PCT Pub. Date: May 7, 2020

(65) Prior Publication Data
US 2021/0371451 A1 Dec. 2, 2021

(30) Foreign Application Priority Data

Nov. 1, 2018 (JP) .............................. JP2018-206292

(51) Int. Cl.
*C07H 21/02* (2006.01)
*C07H 1/06* (2006.01)

(52) U.S. Cl.
CPC ............... *C07H 21/02* (2013.01); *C07H 1/06* (2013.01); *C07B 2200/13* (2013.01)

(58) Field of Classification Search
None
See application file for complete search history.

(56) References Cited

U.S. PATENT DOCUMENTS

| 2002/0048610 A1 | 4/2002 | Cima et al. |
| 2017/0096439 A1 | 4/2017 | Tanaka et al. |

FOREIGN PATENT DOCUMENTS

| JP | 2003-519698 A | 6/2003 |
| WO | WO-2015/137469 A1 | 9/2015 |

OTHER PUBLICATIONS

Newman, Org. Process Res. Dev. 2013, 17, 457-471. (Year: 2013).*
"API form screening and selection in drug discovery stage," Pharm. Stage 6(10):20-25 (2007) (8 pages).
"Crystallization of polymorphs and pseudo-polymorphs and its control," Pharm. Stage 6(10):48-53 (2007) (8 pages).
"Setting of new drug standards and test methods," Pharm. Invest. No. 568, <https://www.pmda.go.jp/files/000156301.pdf>, retrieved Apr. 26, 2021 (2001).
Amiot et al., "New approach for the synthesis of c-di-GMP and its analogues," Synthesis 24:4230-4236 (2006).
Byrn et al., "Pharmaceutical solids: a strategic approach to regulatory considerations," Pharm. Res. 12(7):945-954 (1995).
Gaffney et al., "Synthesis of biotinylated c-di-GMP and c-di-AMP using click conjugation," available in PMC Jan. 1, 2014, published in final edited form as: Nucleosides Nucleotides Nucleic Acids 32(1):1-16 (2013) (14 pages).
International Search Report dated Jan. 21, 2020, for PCT International Application No. PCT/JP2019/042706, Takamatsu et al., "Cyclic-di-AMP Sodium Salt Crystal," filed Oct. 31, 2019 (7 pages).
Kamegaya et al., "Identification of a *Streptococcus pyogenes* SF370 gene involved in production of c-di-AMP," Nagoya J. Med. Sci. 73(1-2):49-57 (2011).
Kawaguchi et al., "Drug and crystal polymorphism," J. Hum. Env. Eng. 4(2):310-317 (2002).
Witte et al., "Structural biochemistry of a bacterial checkpoint protein reveals diadenylate cyclase activity regulated by DNA recombination intermediates," Mol. Cell. 30(2):167-178 (2008).
Woodward et al., "c-di-AMP secreted by intracellular Listeria monocytogenes activates a host type I interferon response," available in PMC Aug. 16, 2011, published in final edited form as: Science 328(5986):1703-1705 (2010) (7 pages).
Yamano, "Approach to crystal polymorph in process research of new drug," J. Syn. Org. Chem., Japan 65(9):907-913 (2007) (7 pages).

* cited by examiner

*Primary Examiner* — Layla D Berry
(74) *Attorney, Agent, or Firm* — Clark & Elbing LLP; Susan M. Michaud

(57) ABSTRACT

A lyophilized product of cyclic-di-AMP requires special production equipment and is thus not suitable for large-scale production. Crystals of cyclic-di-AMP free acid are unstable under severe conditions at 105° C. Then, the present invention addresses the problem of providing a cyclic-di-AMP crystal that can be easily acquired in a large amount and is very stable under the severe conditions at 105° C. Crystals of c-di-AMP sodium salt according to the present invention are extremely stable even under the severe conditions at 105° C. Further, the crystals of c-di-AMP sodium salt according to the present invention can be prepared in a large amount by a simple process including adjusting a c-di-AMP aqueous solution at pH 5.2-12.0 and then adding an organic solvent thereto.

3 Claims, 9 Drawing Sheets

[Fig. 1]
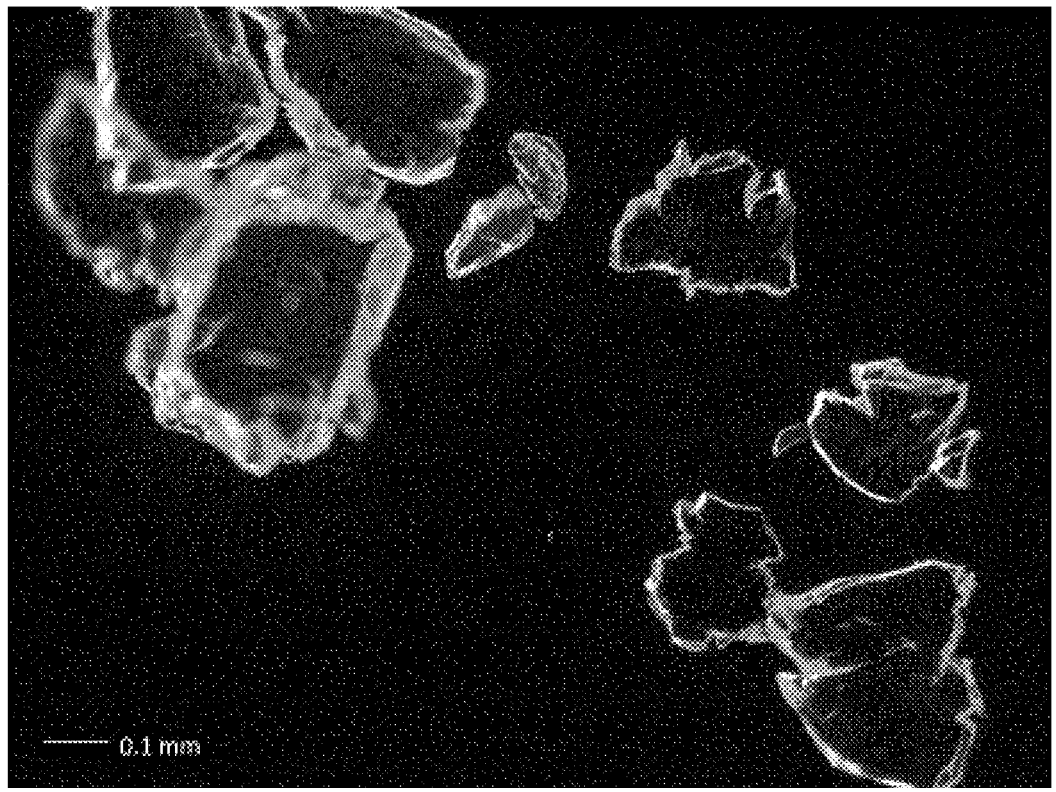
[Fig. 2]
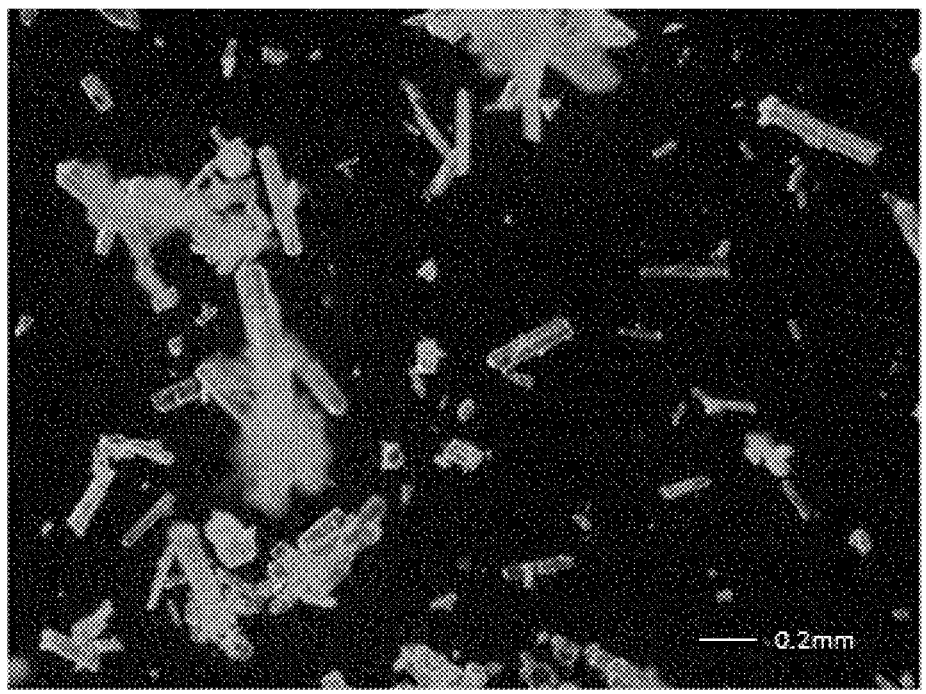

[Fig. 3]
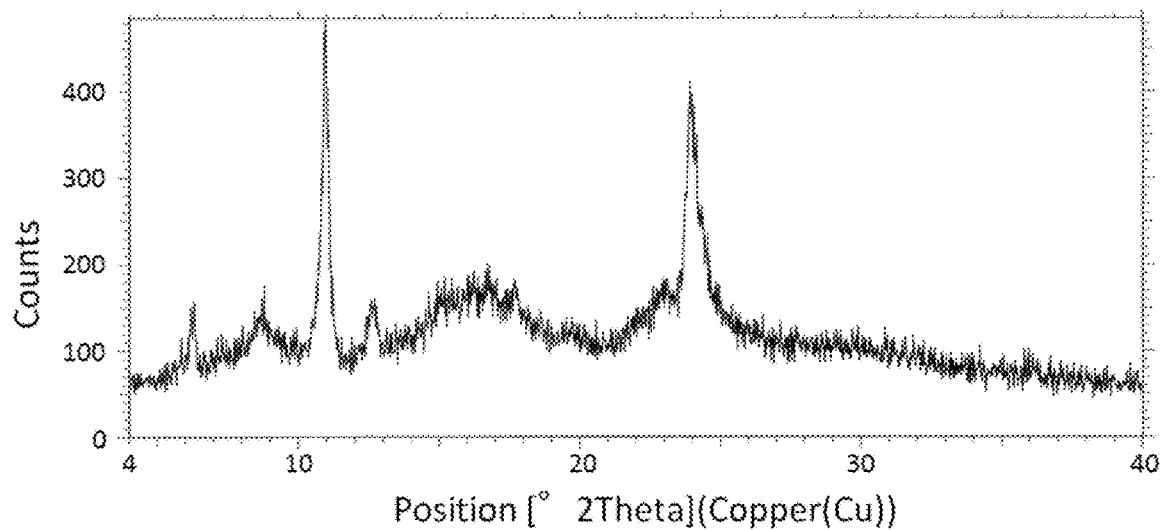
[Fig. 4]
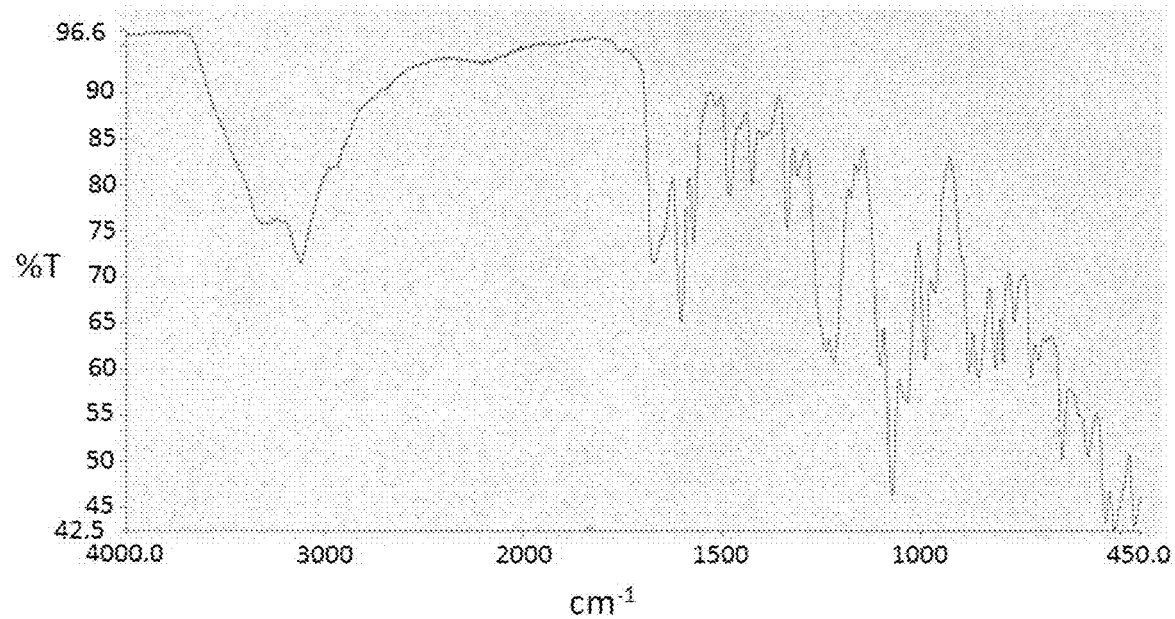

[Fig. 5]
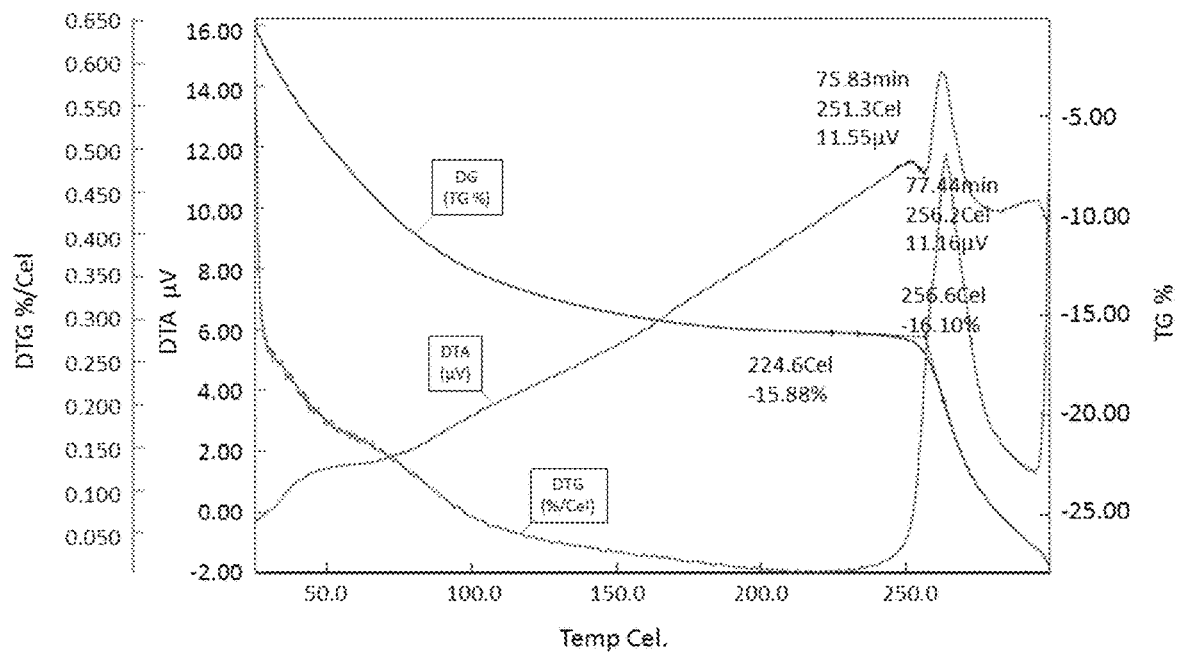
[Fig. 6]
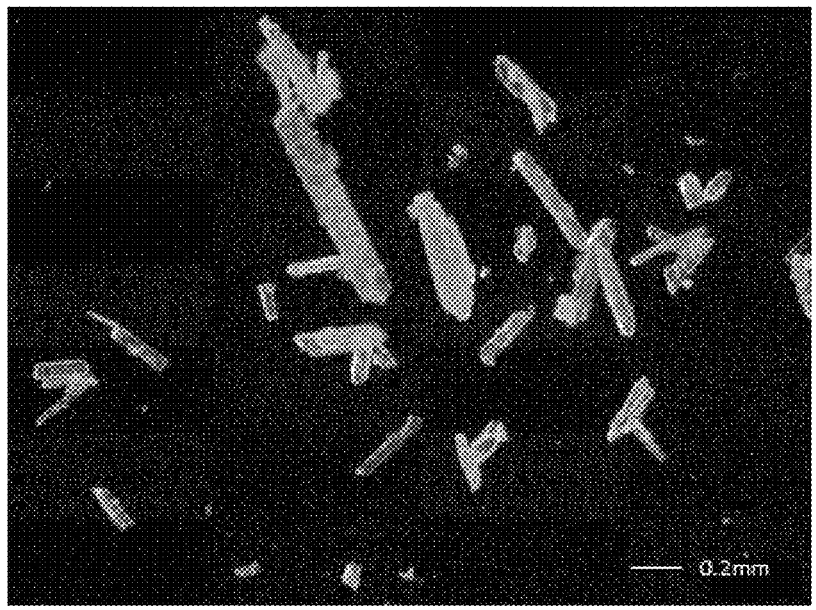

[Fig. 7]
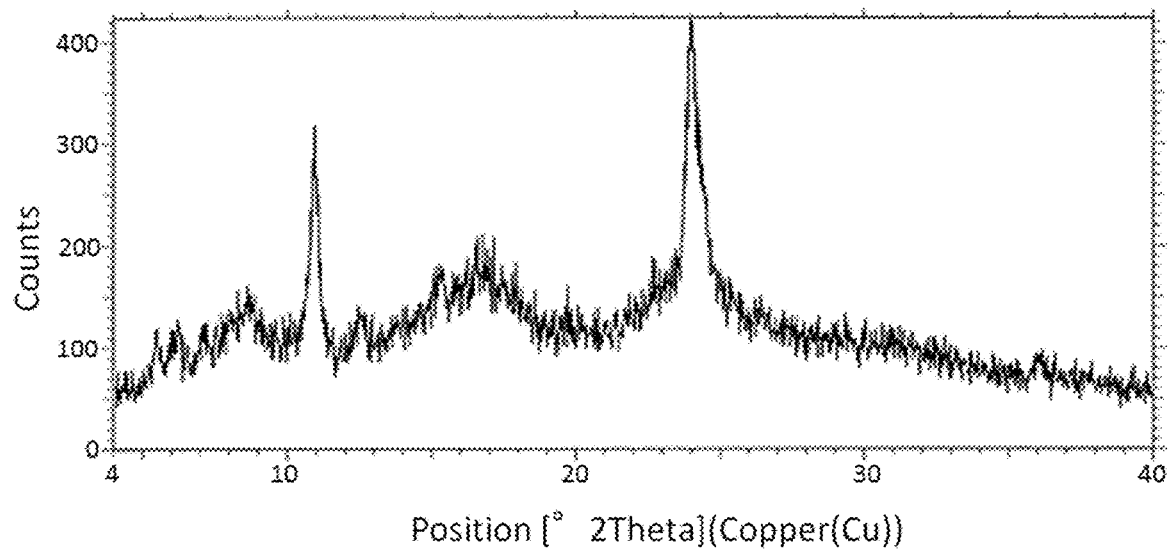
[Fig. 8]
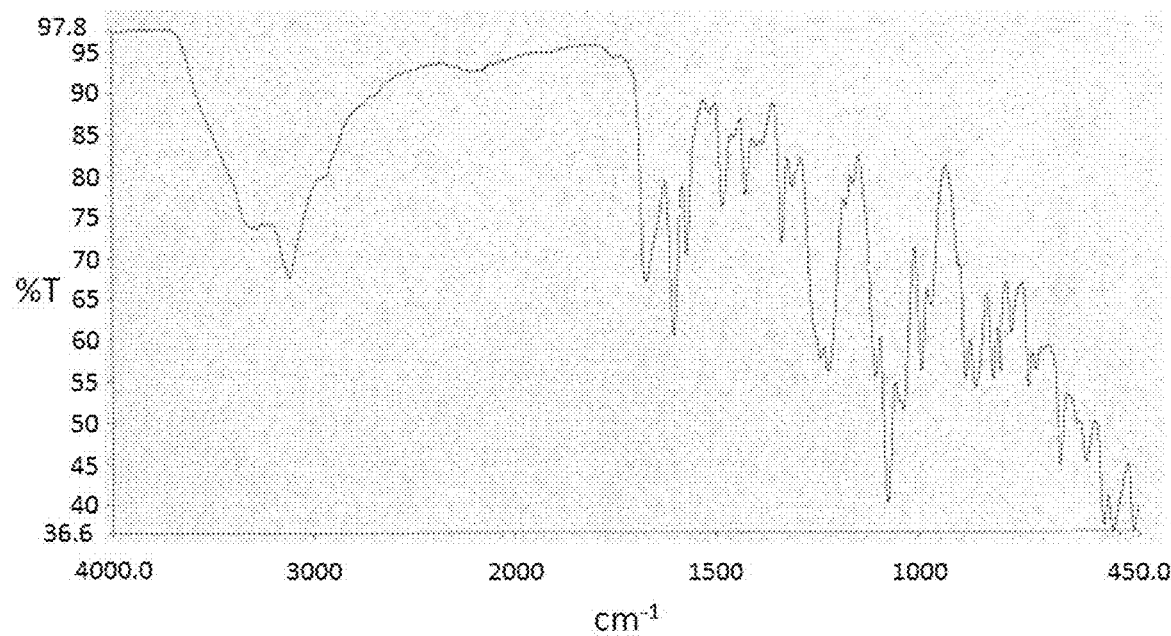

[Fig. 9]
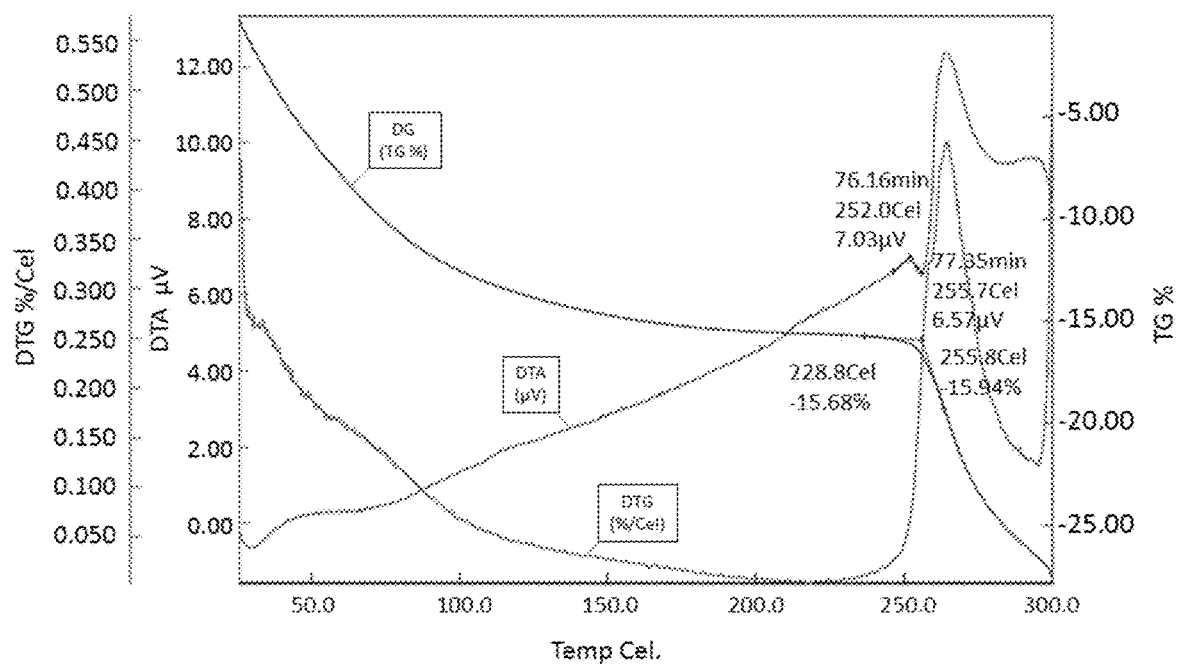
[Fig. 10]
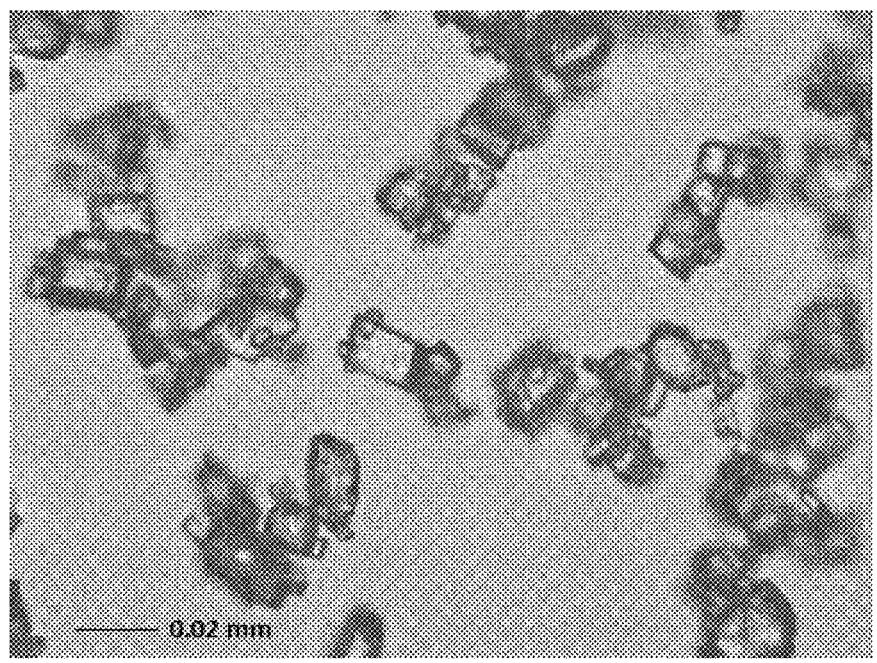

[Fig. 11]
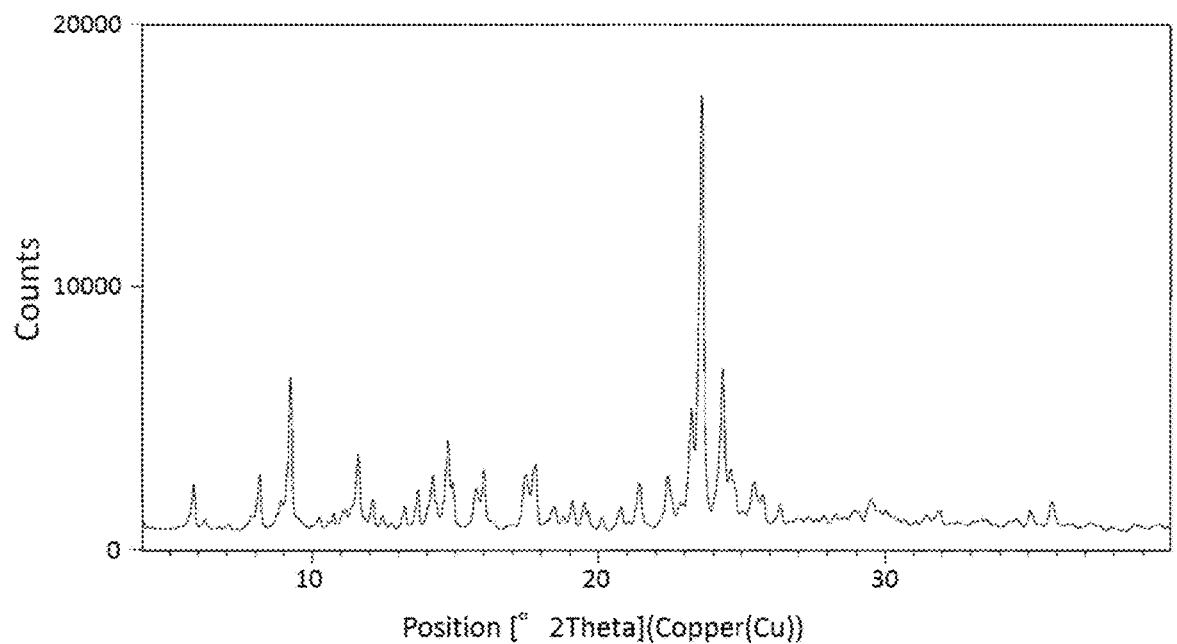
[Fig. 12]
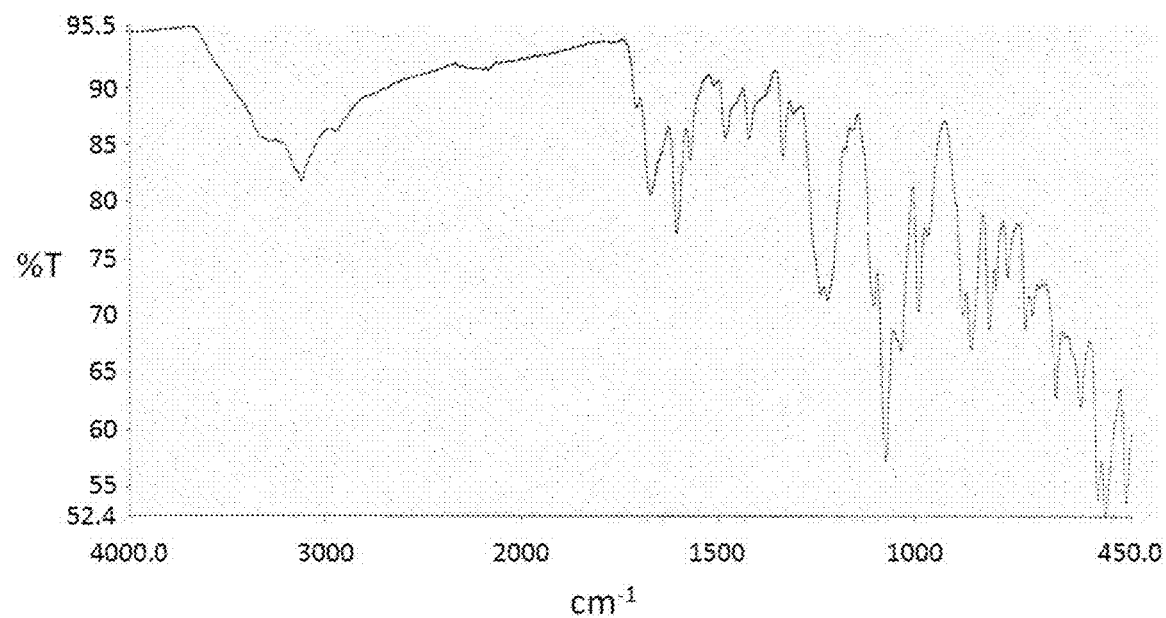

[Fig. 13]
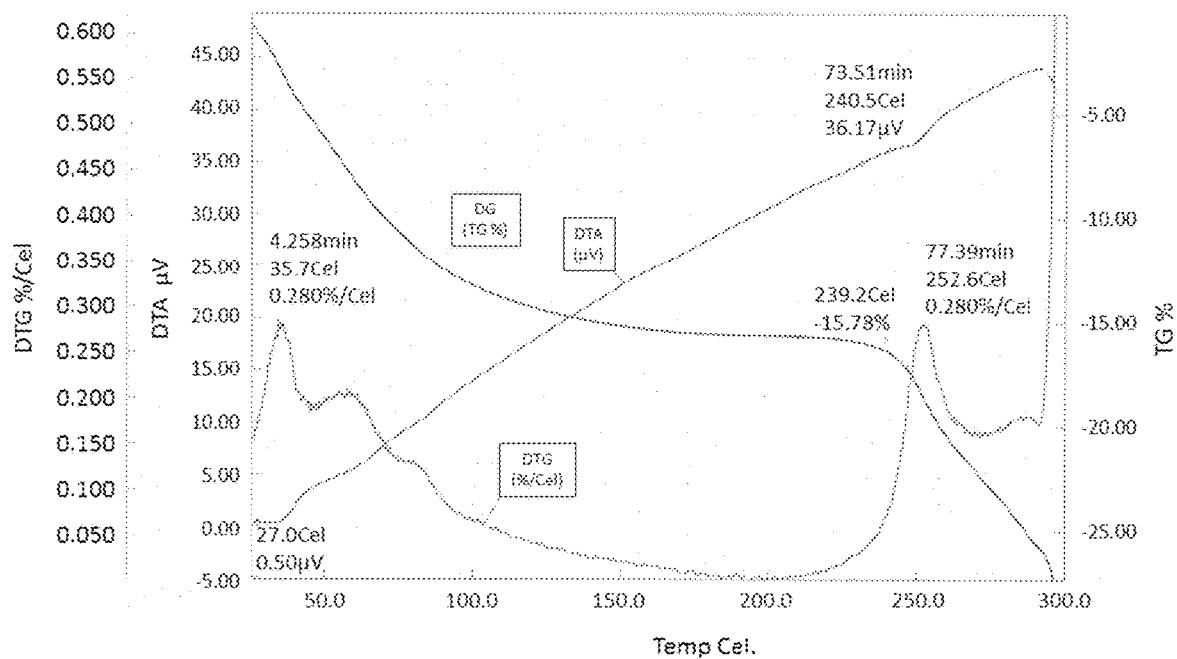
[Fig. 14]
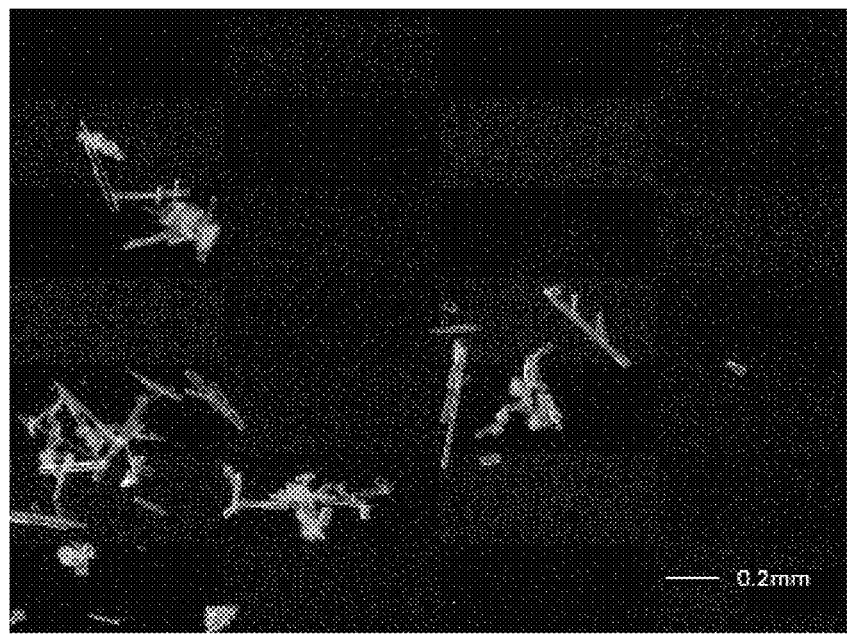

[Fig. 15]
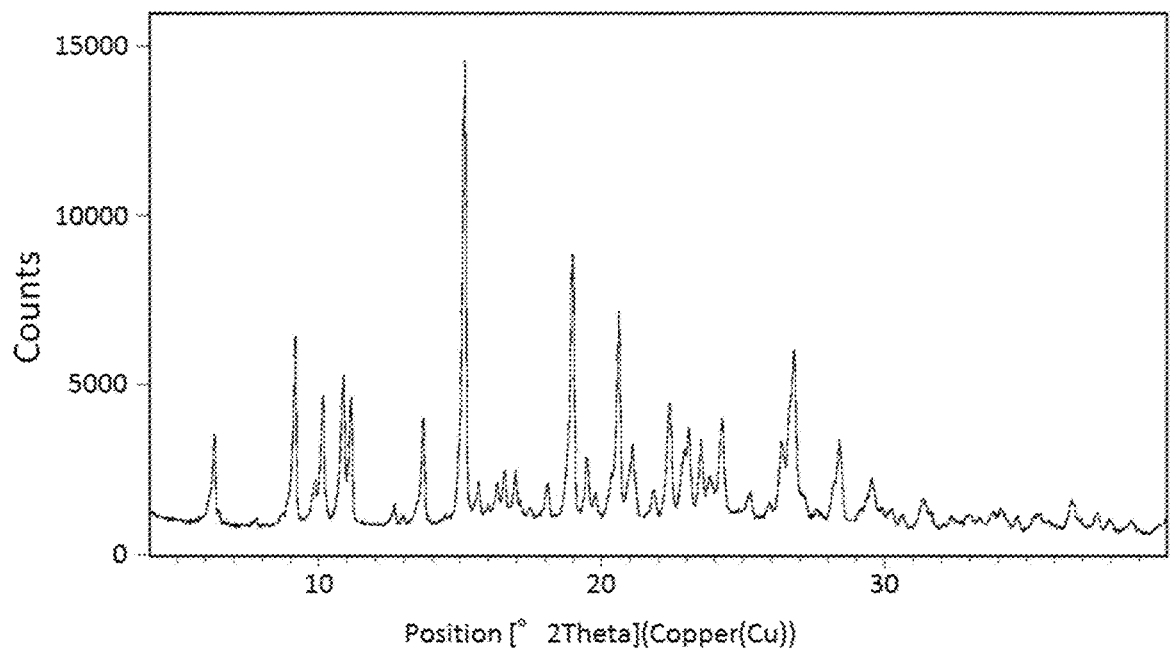
[Fig. 16]
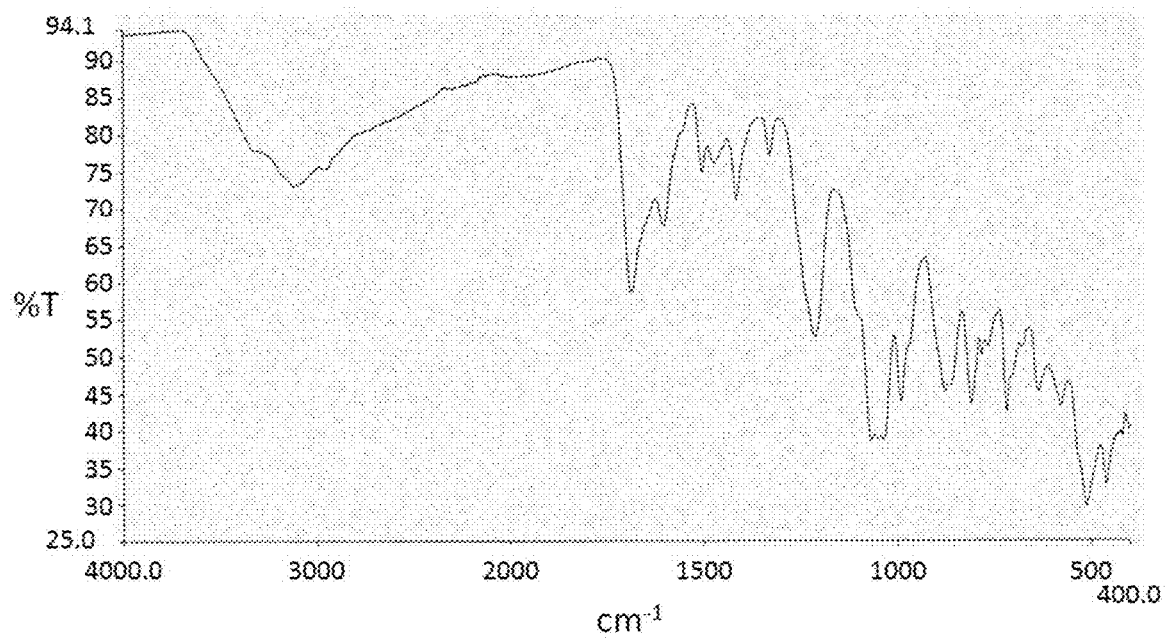

[Fig. 17]
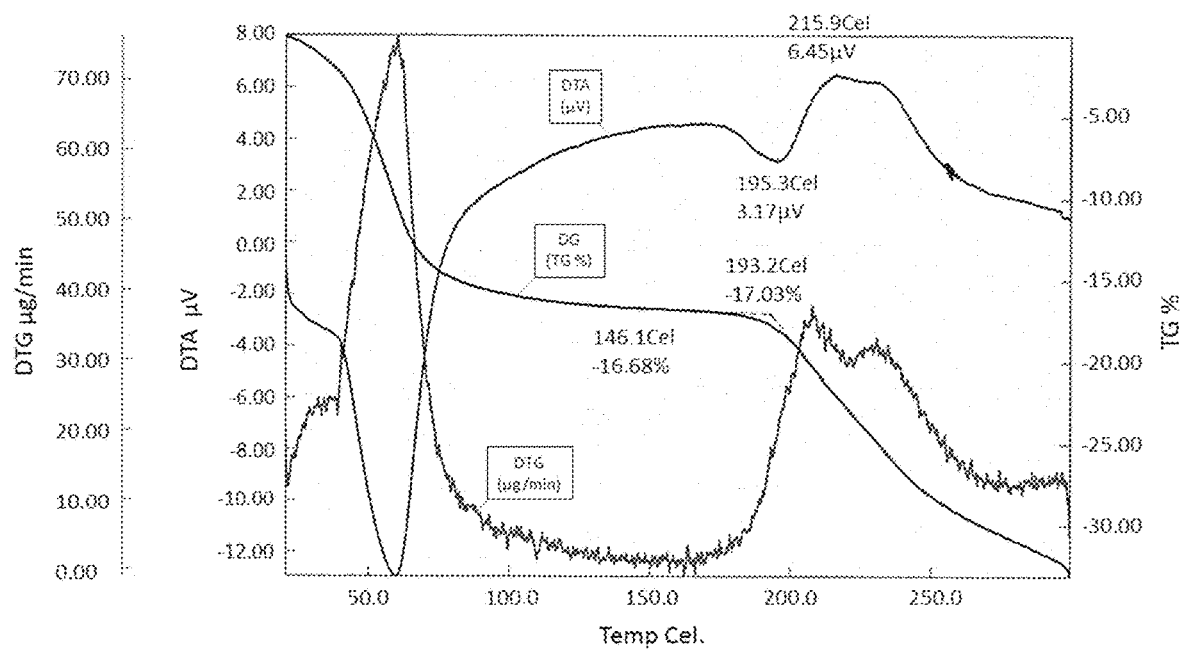
[Fig. 18]
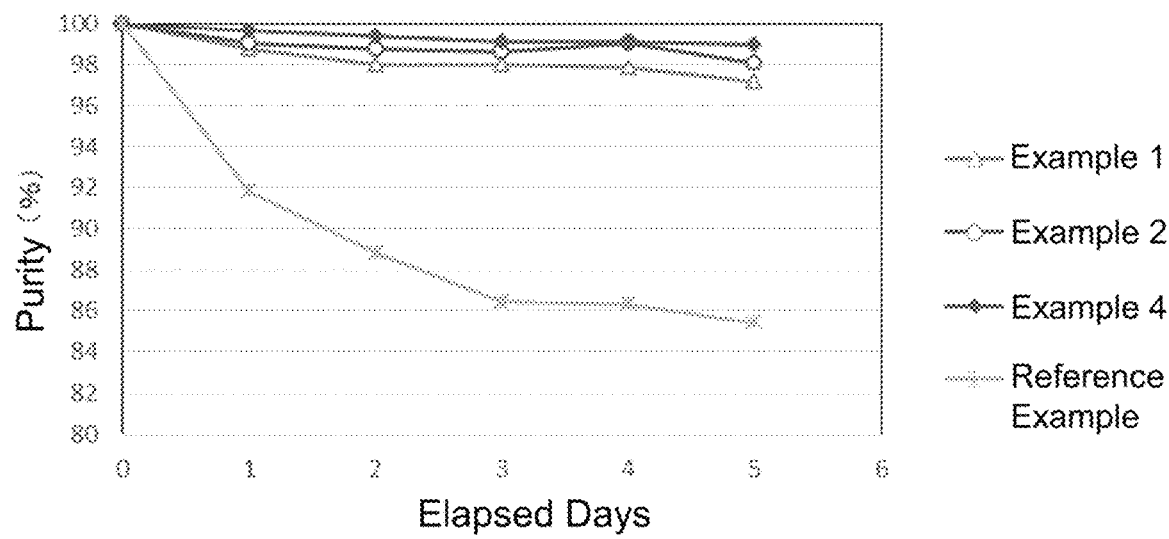

CYCLIC-DI-AMP SODIUM SALT CRYSTAL

TECHNICAL FIELD

The present invention relates to crystals of cyclic-di-AMP sodium salt that can be a useful substance as adjuvant.

BACKGROUND ART

Cyclic-di-AMP (hereinafter, referred to as "c-di-AMP") is a substance discovered as a second messenger in bacteria. A report (Non-Patent Literature 1) has recently shown that this substance can induce type-I interferon and should thus be applicable as a pharmaceutical agent. To date, examples of the c-di-AMP production process known include chemical synthesis processes (Non-Patent Literatures 2 and 3) or enzymatic synthesis processes using *Bacillus*- or *Streptococcus*-derived di-adenylate cyclase (Non-Patent Literatures 4 and 5).

Currently commercially available c-di-AMP is a lyophilized product. Meanwhile, the free acid crystal disclosed in Patent Literature 1 is reportedly only the crystal that has been obtained (Patent Literature 1). Some products are marketed as "crystalline solids". However, the products are amorphous and can be spread without cracking when crushed. Thus, the commercially available crystalline solids cannot be said to be crystals (FIG. 1).

CITATION LIST

Patent Literature

Patent Literature 1: International Publication WO 2015/137469

Non Patent Literature

Non Patent Literature 1: Science, 328, 1703-1705 (2010)
Non Patent Literature 2: SYNTHESIS, 24, 4230-4236 (2006)
Non Patent Literature 3: Nucleosides Nucleotides Nucleic Acids, 32, 1-16 (2013)
Non Patent Literature 4: Molecular Cell, 30, 167-178 (2008)
Non Patent Literature 5: Nagoya J. Med. Sci., 73, 49-57 (2011)

SUMMARY OF INVENTION

Technical Problem

Among commonly known c-di-AMP is a lyophilized product. The lyophilized product needs a lyophilizer during the manufacture. This, itself, causes a limitation in scale-up for mass production. Thus, it has been desirable to develop a process for producing a large amount of the crystal in a simple manner without using a special apparatus such as a lyophilizer.

Here, the present inventors have investigated and found that existing crystals of c-di-AMP free acid are disadvantageous because of decreased stability under severe conditions, for instance, under conditions at 105° C.

Solution to Problem

The present inventors have conducted intensive research on crystallization of c-di-AMP and, as a result, has obtained crystals of c-di-AMP sodium salt for the first time. In this way, the invention has been completed.

Advantageous Effects of Invention

The present inventors have examined and found that crystals of c-di-AMP sodium salt can be obtained by a process including the steps of: (1) adding a base or acid to a c-di-AMP aqueous solution to adjust a pH to 5.2 to 12.0; (2) making the c-di-AMP aqueous solution have an optical density $OD_{257}$ of from 500 to 20000 as measured at a wavelength of 257 nm; (3) heating the c-di-AMP aqueous solution to 30 to 70° C.; (4) adding an organic solvent to the c-di-AMP aqueous solution; and (5) cooling the c-di-AMP aqueous solution to 1 to 30° C. It has been revealed that the resulting crystals of c-di-AMP sodium salt are extremely stable even under severe conditions at 105° C. Further, the crystals of c-di-AMP sodium salt according to the invention have exhibited a higher solubility than existing crystals of c-di-AMP free acid.

For crystallization, the pH in step (1) is particularly critical. The crystallization itself is difficult under acidic conditions at a pH of less than 5.2. Even if the crystals are obtained, the yield is low and not preferable. By contrast, if the pH is 5.2 or higher, it is possible to easily obtain only crystals of sodium salt. Hence, this process for producing a crystal of c-di-AMP sodium salt according to the invention is a process suitable for mass production of the crystal of c-di-AMP salt.

BRIEF DESCRIPTION OF DRAWINGS

FIG. 1 is a photograph showing how a commercially available c-di-AMP crystalline solid looked when spread.

FIG. 2 shows a crystal image of crystals α of c-di-AMP sodium salt as obtained in Example 1.

FIG. 3 shows an X-ray diffraction spectrum of the crystal α of c-di-AMP sodium salt as obtained in Example 1.

FIG. 4 shows an infrared absorption spectrum of the crystal α of c-di-AMP sodium salt as obtained in Example 1.

FIG. 5 shows the results of thermogravimetry/differential thermal analysis of the crystal α of c-di-AMP sodium salt as obtained in Example 1.

FIG. 6 shows a crystal image of crystals α of c-di-AMP sodium salt as obtained in Example 2.

FIG. 7 shows an X-ray diffraction spectrum of the crystal α of c-di-AMP sodium salt as obtained in Example 2.

FIG. 8 shows an infrared absorption spectrum of the crystal α of c-di-AMP sodium salt as obtained in Example 2.

FIG. 9 shows the results of thermogravimetry/differential thermal analysis of the crystal α of c-di-AMP sodium salt as obtained in Example 2.

FIG. 10 shows a crystal image of crystals 13 of c-di-AMP sodium salt as obtained in Example 4.

FIG. 11 shows an X-ray diffraction spectrum of the crystal β of c-di-AMP sodium salt as obtained in Example 4.

FIG. 12 shows an infrared absorption spectrum of the crystal β of c-di-AMP sodium salt as obtained in Example 4.

FIG. 13 shows the results of thermogravimetry/differential thermal analysis of the crystal β of c-di-AMP sodium salt as obtained in Example 4.

FIG. 14 is a crystal image of crystals of c-di-AMP free acid.

FIG. 15 is an X-ray diffraction spectrum of the crystal of c-di-AMP free acid.

FIG. 16 is an infrared absorption spectrum of the crystal of c-di-AMP free acid.

FIG. 17 shows the results of thermogravimetry/differential thermal analysis of the crystal of c-di-AMP free acid.

FIG. 18 shows the results of testing stability, under severe conditions (at 105° C.), of the crystals of c-di-AMP free acid as obtained in Reference Example, the crystals α of sodium salt as obtained in Example 1 or 2, and the crystals 13 of sodium salt as obtained in Example 4.

DESCRIPTION OF EMBODIMENTS

The invention provides crystals of cyclic-di-AMP sodium salt represented by the following structural formula. X in the following structural formula represents a hydrogen atom (H) or a sodium atom (Na); and at least one of two X in the formula is a sodium atom.

[Chemical Formula 1]

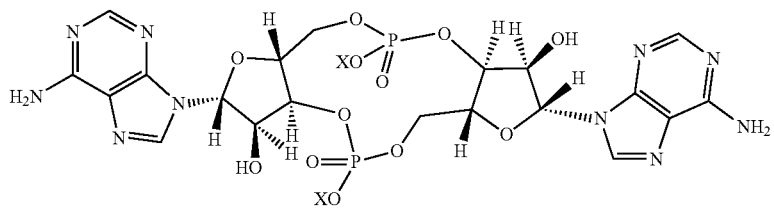

The crystal of c-di-AMP sodium salt can take two forms depending on the pH of c-di-AMP aqueous solution during preparation. Hereinafter, the crystal of c-di-AMP obtained when the pH ranges from 6.0 to 12.0 during preparation is defined as a crystal α and the crystal obtained when the pH ranges from 5.2 to 6.0 is defined as a crystal β.

When the crystal α of c-di-AMP sodium salt according to the invention is analyzed by atomic absorption spectrophotometry, the sodium content ranges from 6.2 to 6.8. This reveals that the abundance ratio of sodium atom per c-di-AMP molecule in the crystal α is 2.

The crystal α of c-di-AMP sodium salt according to the invention can be obtained as a prismatic crystal (see FIGS. 2 and 6).

In addition, the crystal α of sodium salt according to the invention is analyzed with a powder X-ray diffractometer using Cu-Kα radiation. Then, there are characteristic peaks of diffraction angle (2θ) at or near 10.9 and 23.9(°) as demonstrated in Examples below (see FIGS. 3 and 7).

Note that generally speaking, the diffraction angles (2θ) in powder X-ray diffraction may include less than 5% error. Examples of the crystal α of sodium salt according to the invention include crystals with perfectly matched diffraction angle peaks in the powder X-ray diffraction as well as crystals with the diffraction angle peaks matched within less than 5% error. For instance, in the powder X-ray diffraction, there are characteristic peaks of diffraction angle (2θ) at 10.9±0.5 and 23.9±1.2(°).

When an infrared absorption spectrum of the crystal α of sodium salt according to the invention is measured, there are characteristic peaks at or near 3118, 1604, 1221, and 1074 (cm$^{-1}$) (see FIGS. 4 and 8).

Note that when an infrared absorption spectrum is measured, in general, less than 2 (cm$^{-1}$) error may be included. Examples of the crystal α of sodium salt according to the invention include crystals with peak positions perfectly matched to the above numbers in the infrared absorption spectrum as well as crystals with the peaks matched within less than 2 cm$^{-1}$ error. When an infrared absorption spectrum thereof is measured, for instance, there are characteristic peaks at 3118±1.9, 1604±1.9, 1221±1.9, and 1074±1.9 (cm$^{-1}$).

When the crystal α of sodium salt according to the invention is analyzed with a thermogravimetry/differential thermal analysis (TG/DTA) device (at a programming rate of 5° C./min), there is an endothermic peak at or near 255° C. (see FIGS. 5 and 9).

When the crystal β of c-di-AMP sodium salt according to the invention is analyzed by atomic absorption spectrophotometry, the sodium content ranges from 4.7 to 5.2. This reveals that the abundance ratio of sodium atom per c-di-AMP molecule in the crystal β is 1.5.

The crystal β of c-di-AMP sodium salt according to the invention can be obtained as a cubic crystal (see FIG. 10).

In addition, the crystal β of sodium salt according to the invention is analyzed with a powder X-ray diffractometer using Cu-Kα radiation. Then, there are characteristic peaks of diffraction angle (2θ) at or near 9.3, 23.6, and 24.3(°) as demonstrated in Examples below (see FIG. 11).

Note that generally speaking, the diffraction angles (2θ) in powder X-ray diffraction may include less than 5% error. Examples of the crystal β of sodium salt according to the invention include crystals with perfectly matched diffraction angle peaks in the powder X-ray diffraction as well as crystals with the diffraction angle peaks matched within less than 5% error. For instance, in the powder X-ray diffraction, there are characteristic peaks of diffraction angle (2θ) at 9.3±0.5, 23.6±1.2, and 24.3±1.2(°).

When an infrared absorption spectrum of the crystal β of sodium salt according to the invention is measured, there are characteristic peaks at or near 3119, 1606, 1222, and 1074 (cm$^{-1}$) (see FIG. 12).

Note that when an infrared absorption spectrum is measured, in general, less than 2 (cm$^{-1}$) error may be included. Examples of the crystal β of sodium salt according to the invention include crystals with peak positions perfectly matched to the above numbers in the infrared absorption spectrum as well as crystals with the peaks matched within less than 2 cm$^{-1}$ error. When an infrared absorption spectrum thereof is measured, for instance, there are characteristic peaks at 3119±1.9, 1606±1.9, 1222±1.9, and 1074±1.9 (cm$^{-1}$).

When the crystal β of sodium salt according to the invention is analyzed with a thermogravimetry/differential thermal analysis (TG/DTA) device (at a programming rate of 5° C./min), there is an endothermic peak at or near 239° C. (see FIG. 13).

When the purity of crystals of cyclic-di-AMP sodium salt is determined by high performance liquid chromatography, the purity is 97% or higher and preferably 99% or higher. Further, the crystals of c-di-AMP sodium salt according to the invention exhibit a higher solubility than existing crystals of c-di-AMP free acid.

Next, a process for producing a crystal of c-di-AMP sodium salt in the invention will be described. Here, c-di-AMP to be crystallized may be synthesized by a known procedure such as an enzymatic synthesis process or a chemical synthesis process. The synthesis should follow an existing protocol. For instance, the protocols described in Non-Patent Literatures 2 to 5 may be used. After the reaction, c-di-AMP produced in the reaction solution may be purified using active carbon or reverse-phase chromatography etc.

The crystals of sodium salt according to the invention may be obtained by adjusting a c-di-AMP aqueous solution at pH 5.2 to 12.0 and adding an organic solvent.

When the pH of the c-di-AMP aqueous solution is from 5.2 to 6.0, the resulting crystal of sodium salt is a crystal β. When the pH is from 6.0 to 12.0, the resulting crystal of sodium salt is a crystal α.

The case of the pH at less than 5.2 results in precipitation in aqueous solution when a highly concentrated c-di-AMP aqueous solution is tried to be prepared. This makes it difficult to obtain a pure crystal of c-di-AMP sodium salt. To avoid the precipitation, the concentration of c-di-AMP aqueous solution may be lowered. In this case, none or just a tiny amount of crystal of c-di-AMP sodium salt can be obtained. This makes it impossible to efficiently produce any crystal. As a result, the pH has to be 5.2 or higher in order to efficiently prepare a crystal of c-di-AMP salt at an industrially available level.

To obtain the crystal at a higher yield, the above crystallization process preferably includes the steps of: (1) adding a base or acid to a c-di-AMP aqueous solution to adjust a pH to 5.2 to 12.0; (2) making the c-di-AMP aqueous solution have an optical density $OD_{257}$ of from 500 to 20000 as measured at a wavelength of 257 nm; (3) heating the c-di-AMP aqueous solution to 30 to 70° C.; (4) adding an organic solvent to the c-di-AMP aqueous solution; and (5) cooling the c-di-AMP aqueous solution to 1 to 30° C.

The pH of the c-di-AMP aqueous solution in the above step (1) may range from 5.2 to 12.0. This enables a crystal of c-di-AMP sodium salt to be obtained. However, from the viewpoint of easy-to-prepare highly concentrated aqueous solution, the pH is preferably 5.4 or higher and more preferably 5.6 or higher. Further, when the crystal is dissolved, the pH of the aqueous solution may be at or near the neutral point. In this case, the utility is high. Thus, the pH of the c-di-AMP aqueous solution is preferably from 7.0 to 11.0, more preferably from 7.0 to 10.0, and still more preferably from 7.0 to 8.5. In this case, an organic solvent may be added to produce a crystal α.

Examples of the acid used in step (1) include, but are not limited to, hydrochloric acid, sulfuric acid, or nitric acid. Examples of the base used include, but are not limited to, sodium hydroxide or sodium acetate. It is preferable to gently add the acid or base so as to prevent amorphous from being precipitated or to prevent crystals from being rapidly precipitated after the rapid addition.

In the above step (2), the optical density $OD_{257}$ of the c-di-AMP aqueous solution as measured at a wavelength of 257 nm may be 500 or higher. In this case, an organic solvent may be added to produce a crystal. Since the additive amount of the organic solvent as required to precipitate the crystal may be decreased, the optical density is preferably 1000 or higher, more preferably 2000 or higher, and still more preferably 3000 or higher. Meanwhile, in the case of highly concentrated c-di-AMP aqueous solution, the viscosity of the solution may be increased, and as a result of which the handling performance deteriorates. Thus, the optical density $OD_{257}$ of the c-di-AMP aqueous solution as measured at a wavelength of 257 nm is preferably 20000 or less, more preferably 15000 or less, and still more preferably 10000 or less.

In the above step (3), the c-di-AMP aqueous solution is heated to a temperature of from 30 to 70° C. As the difference in the temperature from the time of cooling in step (5) increases, the crystal is more likely to precipitate. Thus, the temperature of the aqueous solution in step (3) is preferably 40° C. or higher and more preferably 50° C. or higher.

The c-di-AMP aqueous solution prior to the organic solvent addition used in the crystal acquisition step in the invention may contain an organic solvent to the extent to which no crystal precipitates. From the viewpoint of preventing unexpected crystallization, the content of the organic solvent is preferably 30% (v/v) or less, more preferably 20% (v/v) or less, still more preferably 10% (v/v) or less, and still more preferably 5% (v/v) or less. It is still more preferable that substantially no organic solvent is included.

Examples of the organic solvent used in step (4) include, but are not limited to, alcohols containing 6 or less carbon atoms such as methanol and ethanol, ketones such as acetone, ethers such as dioxane, nitriles such as acetonitrile, or amides such as dimethylformamide. From the viewpoint of availability and safety, in particular, it is preferable to use alcohols containing 6 or less carbon atoms. Among them, it is preferable to use ethanol.

In the above step (5), the c-di-AMP aqueous solution is cooled to 1 to 30° C. As the difference in the temperature from the time of heating in step (3) increases, the crystal is more likely to precipitate. Thus, the temperature of the aqueous solution in step (5) is preferably 20° C. or lower and more preferably 10° C. or lower.

Further, the above steps (1) to (5) are preferably carried out in sequence. However, any continuous steps may be carried out at the same time, if appropriate.

The crystals of c-di-AMP sodium salt as produced by the above production process may be filtered and then dried to yield a product. For the drying, it is possible to use, if appropriate, a procedure such as vacuum drying.

EXAMPLES

Hereinafter, the invention will be specifically described by referring to Examples. It is clear that the invention, however, is not limited to them.

(Example 1) to Produce Crystal α of c-Di-AMP Sodium Salt at pH 8.2

First, c-di-AMP was enzymatically synthesized and then purified in accordance with a known procedure.

The purified c-di-AMP solution (102 mL) with an $OD_{257}$ of 4710 and at pH 8.2 was heated to 40° C. Next, 142 mL of 99.5% (w/w) ethanol was gently added while stirring. The mixture was cooled until the liquid temperature reached 4° C. to precipitate crystals. The resulting crystals so precipitated were filtered through a basket separator to yield wet crystals. The wet crystals were dried at 30° C. for 2 h to give 9.8 g of dry crystals.

(A) To Analyze Form of Sodium Salt.

When analyzed by atomic absorption spectrophotometry, the crystal of c-di-AMP sodium salt in this Example had a sodium content of 6.4%. This indicated that the abundance of sodium atom per c-di-AMP molecule was 2.0. This thus revealed that the crystal α of c-di-AMP sodium salt in this Example had a form of disodium salt.

(B) Purity Test

The purity of the c-di-AMP sodium salt in the crystal α obtained in Example 1 was analyzed by high performance liquid chromatography. As a result, the purity of c-di-AMP was 100%. Note that the high performance liquid chromatography was performed under the following conditions.

(Conditions)

Column: Hydrosphere C18 (manufactured by YMC, Inc.)

Eluent: 0.1 M TEA-P (pH 6.0)+4.5% ACN

Detection method: detection at UV260 nm (C) Crystal Form

FIG. 2 shows an image of crystals a of c-di-AMP sodium salt in this Example. FIG. 2 shows and has revealed that the crystals α of c-di-AMP sodium salt each have a prismatic crystal form.

(D) Powder X-Ray Diffraction

A crystal α of c-di-AMP sodium salt in this Example was subjected to X-ray diffraction spectrometry using an X-ray diffractometer X'Pert PRO MPD (Spectris) under the following measurement conditions.

(Measurement Conditions)

Target: Cu

X-ray tube current: 40 mA

X-ray tube voltage: 45 kV

Scanning range: 2θ=4.0 to 40.0°

Pretreatment: pulverization using an agate mortar

FIG. 3 and Table 1 show that the crystal α of c-di-AMP sodium salt in this Example had characteristic peaks of diffraction angle (2θ) at or near 6.2, 10.9, 12.6, and 23.9(°), in particular 10.9 and 23.9(°).

TABLE 1

| 2θ (°) | Relative Intensity (%) |
|---|---|
| 6.2 | 29.4 |
| 10.9 | 100 |
| 12.6 | 31.1 |
| 23.9 | 81.7 |

(E) Infrared Absorption Spectrum

A crystal α of c-di-AMP sodium salt in this Example was subjected to infrared absorption spectroscopy using a Fourier transform infrared spectrophotometer Spectrum One (Perkin Elmer) and the Attenuated Total Reflectance (ATR) method.

The crystal α of c-di-AMP sodium salt in this Example had characteristic peaks at or near 3119, 1604, 1220, and 1073 ($cm^{-1}$). FIG. 4 shows the results.

(F) Differential Scanning calorimetry

When a crystal α of c-di-AMP sodium salt in this Example was analyzed with a thermogravimetry/differential thermal analysis (TG/DTA) device (at a programming rate of 5° C./min), there was an endothermic peak at or near 255° C. (FIG. 5).

(Example 2) to Produce Crystal α of c-Di-AMP Sodium Salt at pH 10.0

First, c-di-AMP was enzymatically synthesized and then purified in accordance with a known procedure.

The purified c-di-AMP solution (50 mL) with an $OD_{257}$ of 6600 and at pH 10.0 was heated to 40° C. Next, 45 mL of ethanol was gently added while stirring. The mixture was cooled until the liquid temperature reached 4° C. to precipitate crystals. The resulting crystals so precipitated were filtered through a membrane filter (3 μm) to yield wet crystals. The wet crystals were dried at 20° C. for 1.5 h to give 7 g of dry crystals.

(A) to Analyze Form of Sodium Salt.

When analyzed by atomic absorption spectrophotometry, the crystal α of c-di-AMP sodium salt in this Example had a sodium content of 6.6%. This indicated that the abundance of sodium atom per c-di-AMP molecule was 2.0. This thus revealed that the crystal α of c-di-AMP sodium salt in this Example had a form of disodium salt.

(B) Purity Test

The purity of the c-di-AMP sodium salt in the crystal α obtained in Example 2 was analyzed by high performance liquid chromatography. As a result, the purity of c-di-AMP was 100%. Note that the high performance liquid chromatography was performed under the following conditions.

(Conditions)

Column: Hydrosphere C18 (manufactured by YMC, Inc.)

Eluent: 0.1 M TEA-P (pH 6.0)+4.5% ACN

Detection method: detection at UV260 nm (C) Crystal Form

FIG. 6 shows an image of crystals α of c-di-AMP sodium salt in this Example. FIG. 6 shows and has revealed that the crystals α of c-di-AMP sodium salt each have a prismatic crystal form.

(D) Powder X-Ray Diffraction

A crystal α of c-di-AMP sodium salt in this Example was subjected to X-ray diffraction spectrometry using an X-ray diffractometer X'Pert PRO MPD (Spectris) under the following measurement conditions.

(Measurement Conditions)

Target: Cu

X-ray tube current: 40 mA

X-ray tube voltage: 45 kV

Scanning range: 2θ=4.0 to 40.0°

Pretreatment: pulverization using an agate mortar

FIG. 7 and Table 2 show that the crystal α of c-di-AMP sodium salt in this Example had characteristic peaks of diffraction angle (2θ) at or near 10.9 and 24.0(°).

TABLE 2

| 2θ (°) | Relative Intensity (%) |
|---|---|
| 10.9 | 75 |
| 24.0 | 100 |

(E) Infrared Absorption Spectrum

A crystal α of c-di-AMP sodium salt in this Example was subjected to infrared absorption spectroscopy using a Fourier transform infrared spectrophotometer Spectrum One (Perkin Elmer) and the Attenuated Total Reflectance (ATR) method.

The crystal α of c-di-AMP sodium salt in this Example had characteristic peaks at or near 3118, 1604, 1221, and 1074 ($cm^{-1}$). FIG. 8 shows the results.

(F) Differential Scanning calorimetry

When a crystal α of c-di-AMP sodium salt in this Example was analyzed with a thermogravimetry/differential thermal analysis (TG/DTA) device (at a programming rate of 5° C./min), there was an endothermic peak at or near 255° C. (FIG. 9).

(Example 3) Test for Producing Crystal of c-Di-AMP Sodium Salt at Low pH Range (pH 5.0-6.5)

To determine the pH range allowing for production of a crystal of c-di-AMP sodium salt, a test for producing a crystal at a low pH range (pH 5.0-6.5) was conducted.

First, c-di-AMP was enzymatically synthesized and then purified in accordance with a known procedure.

The purified c-di-AMP was used to prepare a c-di-AMP aqueous solution with an $OD_{257}$ of 2500 and at a pH of 5.0, 5.2, 5.4, 5.6, 5.8, 6.0, or 6.5. Each resulting c-di-AMP solution (0.2 mL) with an $OD_{257}$ of 2500 was heated to 30° C. Next, 1 mL of 99.5% (w/w) ethanol was gently added. The mixture was then tightly sealed and allowed to stand overnight or for several days at 30° C. to precipitate crystals. The resulting crystals so precipitated were filtered through a membrane filter to yield wet crystals.

Table 3 below shows the results obtained. In Table 3 below, the "Crystal" indicates whether or not any crystal was obtained.

○: Crystals were obtained without any problem.

Δ: Although crystals were obtained, the amount was smaller than that at other pH.

x: The aqueous solution was unable to be prepared, and no crystal was thus obtained.

TABLE 3

| | pH | | | | | | |
|---|---|---|---|---|---|---|---|
| | 5.0 | 5.2 | 5.4 | 5.6 | 5.8 | 6.0 | 6.5 |
| Crystal | x | Δ | ○ | ○ | ○ | ○ | ○ |

As shown in the above Table 3, the solubility of c-di-AMP at pH 5.0 was low. Thus, it was impossible at all to prepare a c-di-AMP aqueous solution with an $OD_{257}$ of 2500. Dilution allowed for preparation of a c-di-AMP aqueous solution at a low concentration. However, even when the subsequent operations were likewise carried out, no crystal was obtained. While some crystals were able to be obtained at pH 5.2, the amount was smaller than that at a pH of 5.4 or higher. Crystals were successfully obtained at a pH of 5.4 or higher without any problem.

Any of c-di-AMP crystals obtained at a pH of from 5.4 to less than 6.0 exhibited a cubic appearance and substantially the same characteristics. This indicated the same form. At pH 6.0, the crystals were a mixture of cubic and prismatic crystals. The c-di-AMP crystals obtained at a pH range, i.e., a pH of 6.0 or higher exhibited a prismatic appearance and substantially the same characteristics as the crystals obtained in Example 1 and 2. The above results have demonstrated that when the c-di-AMP aqueous solution has a pH of from 5.2 to 6.0, a c-di-AMP crystal β can be obtained as a form in the Examples; and when the pH ranges from 6.0 to 12.0, a crystal α of c-di-AMP sodium salt can be obtained.

(Example 4) to Produce Crystal 13 of c-Di-AMP Sodium Salt at pH 5.6

First, c-di-AMP was enzymatically synthesized and then purified in accordance with a known procedure.

The purified c-di-AMP solution (15 mL) with an $OD_{257}$ of 3000 and at pH 5.6 was heated to 30° C. Next, 15 mL of ethanol was gently added while stirring. The mixture was cooled until the liquid temperature reached 4° C. to precipitate crystals. The resulting crystals so precipitated were filtered through a membrane filter to yield wet crystals. The wet crystals were dried at 25° C. for 2 h to give 1.0 g of dry crystals.

(A) to Analyze Form of Sodium Salt.

When analyzed by atomic absorption spectrophotometry, the crystal β of c-di-AMP sodium salt in this Example had a sodium content of 5.2%. This revealed that the abundance of sodium atom per c-di-AMP molecule was 1.5.

(B) Purity Test

The purity of the c-di-AMP sodium salt in the crystal β obtained in this Example was analyzed by high performance liquid chromatography. As a result, the purity of c-di-AMP was 100%. Note that the high performance liquid chromatography was performed under the following conditions.

(Conditions)

Column: YMC-Triart C18 (manufactured by YMC, Inc.)

Eluent: 0.1 M TEA-P (pH 6.0)+4.5% ACN

Detection method: detection at UV260 nm (C) Crystal Form

FIG. 10 shows an image of crystals β of c-di-AMP sodium salt in this Example. FIG. 10 shows and has revealed that the crystals 13 of c-di-AMP sodium salt each have a cubic crystal form.

(D) Powder X-Ray Diffraction

A crystal of c-di-AMP sodium salt in this Example was subjected to X-ray diffraction spectrometry using an X-ray diffractometer X'Pert PRO MPD (Spectris) under the following measurement conditions.

(Measurement Conditions)

Target: Cu

X-ray tube current: 40 mA

X-ray tube voltage: 45 kV

Scanning range: 2θ=4.0 to 40.0°

Pretreatment: pulverization using an agate mortar

FIG. 11 and Table 4 show that the crystal β of c-di-AMP sodium salt in this Example had characteristic peaks of diffraction angle (2θ) at or near 9.3, 23.6, and 24.3(°).

TABLE 4

| 2θ (°) | Relative Intensity (%) |
|---|---|
| 9.3 | 34.7 |
| 23.6 | 100 |
| 24.3 | 36.6 |

(E) Infrared Absorption Spectrum

A crystal β of c-di-AMP sodium salt in this Example was subjected to infrared absorption spectroscopy using a Fourier transform infrared spectrophotometer Spectrum One (Perkin Elmer) and the Attenuated Total Reflectance (ATR) method.

The crystal β of c-di-AMP sodium salt in this Example had characteristic peaks at or near 3119, 1606, 1222, and 1074 ($cm^{-1}$). FIG. 12 shows the results.

(F) Differential Scanning calorimetry

When a crystal β of c-di-AMP sodium salt in this Example was analyzed with a thermogravimetry/differential thermal analysis (TG/DTA) device (at a programming rate of 5° C./min), there was an endothermic peak at or near 239° C. (FIG. 13).

(Reference Example) to Produce Crystal of c-Di-AMP Free Acid

First, c-di-AMP was enzymatically synthesized and then purified in accordance with a known procedure.

Crystals of c-di-AMP free acid were obtained from the purified c-di-AMP solution in accordance with the procedure disclosed in Patent Literature 1. Specifically, the c-di-AMP solution (980 mL) with an $OD_{257}$ of 114 was heated to 50° C. Next, 2 N HCl was added portionwise to adjust the pH to 1.8. Then, the mixture was cooled until the liquid temperature reached 4° C. to precipitate crystals. The resulting crystals so precipitated were filtered through a glass filter (G3) to yield wet crystals. The wet crystals were dried at 20° C. for 1 h to give 2.8 g of dry crystals.

(A) Purity Test

The purity of the c-di-AMP free acid in the crystal obtained in the above Reference Example was analyzed by high performance liquid chromatography. As a result, the purity of c-di-AMP was 100%. Note that the high performance liquid chromatography was performed under the following conditions.

(Conditions)
Column: Hydrosphere C18 (manufactured by YMC, Inc.)
Eluent: 0.1 M TEA-P (pH 6.0)+4.5% ACN
Detection method: detection at UV260 nm (B) Crystal Form FIG. 14 is a representative image of crystals of c-di-AMP free acid. The crystals of c-di-AMP free acid each have a needle-shaped crystal form.

(C) Powder X-Ray Diffraction

A crystal of c-di-AMP free acid was subjected to X-ray diffraction spectrometry using an X-ray diffractometer X'Pert PRO MPD (Spectris) under the following measurement conditions.

(Measurement Conditions)
Target: Cu
X-ray tube current: 40 mA
X-ray tube voltage: 45 kV
Scanning range: 2θ=4.0 to 40.0°
Pretreatment: pulverization using an agate mortar FIG. 15 and Table 5 show that the crystal of c-di-AMP free acid disclosed in Patent Literature 1 had characteristic peaks of diffraction angle (2θ) at or near 9.2, 10.2, 10.9, 11.1, 13.7, 15.2, 19.0, 20.6, 22.4, 23.1, 24.3, 26.6, and 26.8(°).

TABLE 5

| 2θ (°) | Relative Intensity (%) |
|---|---|
| 9.2 | 41.9 |
| 10.2 | 28.5 |
| 10.9 | 32.1 |
| 11.1 | 27.9 |
| 13.7 | 23.5 |
| 15.2 | 100 |
| 19 | 59.2 |
| 20.6 | 46.4 |
| 22.4 | 26.8 |
| 23.1 | 21.7 |
| 24.3 | 23.5 |
| 26.6 | 25.6 |
| 26.8 | 38.9 |

(D) Infrared Absorption Spectrum

Patent Literature 1 discloses the results obtained when a crystal of c-di-AMP free acid was subjected to infrared absorption spectroscopy using a Fourier transform infrared spectrophotometer Spectrum One (Perkin Elmer) and the Attenuated Total Reflectance (ATR) method.

The crystal of c-di-AMP free acid disclosed in Patent Literature 1 had characteristic peaks at or near 3087, 1686, 1604, 1504, 1473, 1415, 1328, and 1213 (cm$^{-1}$). FIG. 16 shows the results.

(E) Differential Scanning calorimetry

When a crystal of c-di-AMP free acid disclosed in Patent Literature 1 was analyzed with a thermogravimetry/differential thermal analysis (TG/DTA) device (at a programming rate of 5° C./min), there was an endothermic peak at or near 193° C. (FIG. 17).

(Example 5) to Test Stability of Resulting Crystals Under Conditions at 105° C.

The crystals obtained in the above Example 1, Example 2, Example 4, and Reference Example were allowed to stand under conditions at 105° C. Some crystals were sampled over time, and an aqueous solution was prepared therefrom. Then, the purity of each crystal was analyzed by high performance liquid chromatography. FIG. 18 and Table 6 show the results obtained.

TABLE 6

| | 0 | 1 | 2 | 3 | 4 | 5 | (Day) |
|---|---|---|---|---|---|---|---|
| Example 1 | 100.00 | 98.75 | 97.98 | 97.98 | 97.87 | 97.15 | |
| Example 2 | 100.00 | 99.02 | 98.73 | 98.63 | 99.02 | 98.09 | |
| Example 4 | 100.00 | 99.65 | 99.35 | 99.14 | 99.09 | 98.93 | |
| Reference Example | 100.00 | 91.81 | 88.82 | 86.46 | 86.31 | 85.42 | (%) |

Table 6 has demonstrated that the crystals of c-di-AMP sodium salt according to the invention have a better stability under severe conditions at 105° C. than existing crystals of c-di-AMP free acid. Further, solubilization of the existing crystals of c-di-AMP free acid required stirring. By contrast, the crystals of c-di-AMP sodium salt according to the invention were dissolved rapidly. This has revealed that the crystals of c-di-AMP sodium salt according to the invention exhibit a higher solubility than the existing crystals of c-di-AMP free acid.

The invention claimed is:

1. A crystal α of cyclic-di-AMP sodium salt, comprising characteristic peaks of diffraction angle (2θ) at 10.9±0.5 and 23.9±1.2(°) as measured by powder X-ray diffraction using Cu-Kα radiation.

2. A crystal β of cyclic-di-AMP sodium salt, comprising characteristic peaks of diffraction angle (2θ) at 9.3±0.5, 23.6±1.2, 23.9±1.2(°) as measured by powder X-ray diffraction using Cu-Kα radiation.

3. A process for producing a crystal of cyclic-di-AMP sodium salt, comprising the steps of:
(1) adding a base and/or an acid to a cyclic-di-AMP aqueous solution to adjust the pH of the solution to 5.2 to 12.0;
(2) making the cyclic-di-AMP aqueous solution have an optical density $OD_{257}$ of from 500 to 20000 as measured at a wavelength of 257 nm;
(3) heating the cyclic-di-AMP aqueous solution to 30 to 70° C.;
(4) adding an organic solvent to the cyclic-di-AMP aqueous solution; and (5) cooling the cyclic-di-AMP aqueous solution to 1 to 30° C. to precipitate and obtain a crystal.

\* \* \* \* \*

UNITED STATES PATENT AND TRADEMARK OFFICE
CERTIFICATE OF CORRECTION

PATENT NO. : 11,485,754 B2
APPLICATION NO. : 17/290361
DATED : November 1, 2022
INVENTOR(S) : Misaki Takamatsu et al.

It is certified that error appears in the above-identified patent and that said Letters Patent is hereby corrected as shown below:

In the Claims

Column 12, Line 54, replace "23.9" with --24.3--.

Signed and Sealed this
Twenty-seventh Day of December, 2022

Katherine Kelly Vidal
*Director of the United States Patent and Trademark Office*